US009162082B2

(12) United States Patent
Osanai (10) Patent No.: US 9,162,082 B2
(45) Date of Patent: Oct. 20, 2015

(54) CIRCULAR ACCELERATOR AND PARTICLE BEAM THERAPY APPARATUS

(71) Applicant: Kabushiki Kaisha Toshiba, Minato-ku (JP)

(72) Inventor: Akihiro Osanai, Yokohama (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

(21) Appl. No.: 14/559,111

(22) Filed: Dec. 3, 2014

(65) Prior Publication Data

US 2015/0157881 A1    Jun. 11, 2015

(30) Foreign Application Priority Data

Dec. 9, 2013   (JP) ................................. 2013-254013

(51) Int. Cl.
| | | |
|---|---|---|
| *A61N 5/10* | (2006.01) | |
| *A61B 6/00* | (2006.01) | |
| *H01J 37/30* | (2006.01) | |
| *H01J 37/147* | (2006.01) | |
| *H05H 13/04* | (2006.01) | |
| *H05H 7/10* | (2006.01) | |
| *H05H 7/08* | (2006.01) | |
| *H05H 7/00* | (2006.01) | |

(52) U.S. Cl.
CPC ........... *A61N 5/1077* (2013.01); *H01J 37/1472* (2013.01); *H01J 37/3007* (2013.01); *H05H 7/08* (2013.01); *H05H 7/10* (2013.01); *H05H 13/04* (2013.01); *A61N 2005/1087* (2013.01); *A61N 2005/1095* (2013.01); *H01J 2237/04732* (2013.01); *H01J 2237/152* (2013.01); *H01J 2237/30472* (2013.01); *H05H 2007/005* (2013.01); *H05H 2007/087* (2013.01)

(58) Field of Classification Search
USPC ....... 250/396 R, 492.1, 492.21, 492.3, 505.1; 315/500–507
See application file for complete search history.

(56) References Cited

U.S. PATENT DOCUMENTS

| | | |
|---|---|---|
| 5,073,913 A | 12/1991 | Martin |
| 5,576,602 A | 11/1996 | Hiramoto et al. |

(Continued)

FOREIGN PATENT DOCUMENTS

| | | |
|---|---|---|
| JP | 8-148299 A | 6/1996 |
| JP | 2011 198748 | 10/2011 |
| JP | 2012 22776 | 2/2012 |

OTHER PUBLICATIONS

Extended European Search Report issued Mar. 27, 2015 in Patent Application No. 14196695.2.

*Primary Examiner* — Bernard E Souw (74) *Attorney, Agent, or Firm* — Oblon, McClelland, Maier & Neustadt, L.L.P.

(57) ABSTRACT

One embodiment of a particle circular accelerator 1 includes: a beam deflector for beam injections, bending electromagnets that causes the beam injected from the beam deflector for beam injections to circulate so as to form a circulation orbit, orbit adjusting electromagnets for injected beams that shift the position of each injected beam relative to the center of the circulation orbit of the beam, quadrupole electromagnets and sextupole electromagnets that adjust their respective quantities of magnetic excitation at the time of a beam extraction so as to extract a beam in a resonant region off a stable reason of beams and a beam deflector for beam extractions that takes out the beam extracted from the resonant region to the outside. The circular accelerator 1 injects beams from the inner side thereof and emits beams to the outer side thereof.

14 Claims, 4 Drawing Sheets

(56) References Cited

U.S. PATENT DOCUMENTS

7,122,978 B2 * 10/2006 Nakanishi et al. ............ 315/500
2005/0231138 A1 * 10/2005 Nakanishi et al. ............ 315/500
2015/0038764 A1 * 2/2015 Sugahara et al. ................ 600/1

* cited by examiner

| ENERGY (MeV/u) | 4(injection) | 140 | 230 | 290 | 350 | 400 | 430 |
|---|---|---|---|---|---|---|---|
| BEAM EMITTANCE | 250 | 40.8 | 31.1 | 27.3 | 24.5 | 22.7 | 21.8 |
| ($\pi$ mm · mrad) | 370 | 60.4 | 46.0 | 40.4 | 36.3 | 33.6 | 32.3 |

CIRCULAR ACCELERATOR AND PARTICLE BEAM THERAPY APPARATUS

CROSS REFERENCE TO RELATED APPLICATION

This application is based upon and claims the benefit of priority from Japanese Patent Application No. 2013-254013, filed on Dec. 9, 2013, the entire content of which is incorporated herein by reference.

FIELD

Embodiments described herein relate to a circular accelerator and also to a particle beam therapy apparatus using the same.

BACKGROUND

Generally, particle beams are employed in particle beam therapy apparatus designed to cure cancers by irradiating a high energy beam that is obtained by accelerating protons or charged particles, whichever appropriate. The particle beam therapy apparatus is required to be capable of adjusting the trajectory of the beam irradiated from the apparatus in the patient body according to the body part that needs to be irradiated with the beam and the depth of the body part from the body surface of the patient.

A circular accelerator is mostly employed in the particle beam therapy apparatus. A variable energy irradiation method has been proposed for the circular accelerator to adjust the trajectory of an irradiated beam in a body by changing the beam energy to be emitted.

With this method, for example, the beam to be irradiated is separated from circulating beams by means of a charged particle beam extraction device and subsequently the beam is deflected in the opposite direction by means of another charged particle beam extraction device, which may typically be a septum magnet that provides a greater deflection angle.

Besides, there has been proposed a method of generating a beam to be irradiated by controlling the parameters of the high frequency voltage to be applied to the high frequency accelerator cavity of a circular accelerator to change the output current intensity of charged particles to be extracted from a circulation orbit.

Furthermore, for instance, Japanese Patent Application Laid-Open Publication Nos. 2012-22776 and 2011-198748 describe particle beam therapy apparatus that are different from the above-described ones.

Meanwhile, in the circular accelerator and in the particle beam therapy apparatus, the size (including the vertical width and horizontal width) of a beam that is driven to circulate changes depending on the energy of the beam. Particularly, when a beam having a large size and showing a low energy level is to be extracted and output, a sufficient spatial margin (to be referred to as clearance hereinafter) cannot be satisfactorily secured between the component devices of the circular accelerator and the beam to make it impossible to extract and output a beam on a stable basis. The remedy for this defect will apparently be to increase the clearance in order to reduce the loss of beam due to the component devices and stably extract a beam. Then, however, the remedy is accompanied by a problem that the size of the circular accelerator needs to be increased.

Therefore, the object of the present embodiment is to dissolve the above identified problem by providing a circular accelerator that is compact and can extract and output beams on a stable basis over a wide range of energy and a particle beam therapy apparatus including such a circular accelerator.

BRIEF DESCRIPTION OF THE DRAWINGS

The features and advantages of the present invention will become apparent from the discussion hereinbelow of specific, illustrative embodiments thereof presented in conjunction with the accompanying drawings, in which.

DETAILED DESCRIPTION

According to one embodiment, there is provided a circular accelerator comprising: a beam deflector for beam injections adapted to inject a beam; beam bending electromagnets for forming a circulation orbit by causing the beam injected from the beam deflector for beam injections to circulate; orbit adjusting electromagnets for adjusting the orbit of an injected beam adapted to shift the position of each injected beam relative to the center of the circulation orbit of the beam; beam extraction electromagnets adapted to adjust their respective quantities of magnetic excitation at the time of extraction of a charged particle beam and operate to draw out a charged particle beam in a resonant region located off a stable region of charged particle beams; and a beam deflector for beam extractions adapted to draw out the beam extracted from the resonant region to the outside; the circular accelerator being adapted to inject the beam from the inner side and extract the beam to the outer side of the circular accelerator.

Further, according to another embodiment, there is provided circular accelerator comprising: a beam deflector for beam injections adapted to inject a beam; beam bending electromagnets for forming a circulation orbit by causing a beam injected from the beam deflector for beam injections to circulate; orbit adjusting electromagnets for adjusting the orbit of an injected beam adapted to shift the position of each injected beam relative to the center of the circulation orbit of the beam; beam extraction electromagnets adapted to adjust their respective quantities of magnetic excitation at the time of extraction of a charged particle beam and operate to draw out a charged particle beam in a resonant region located off a stable region of charged particle beams; and a beam deflector for beam extractions adapted to draw out the beam extracted from the resonant region to the outside; the circular accelerator being adapted to inject the beam from the outer side and extract the beam to the inner side of the circular accelerator.

Further, according to another embodiment, there is provided a particle beam therapy apparatus comprising: a circular accelerator having: a beam-deflector for beam injections adapted to inject a beam; beam bending electromagnets for forming a circulation orbit by causing a beam injected from the beam deflector for beam injections to circulate; orbit adjusting electromagnets for adjusting the orbit of an injected beam adapted to shift the position of each injected beam relative to the center of the circulation orbit of the beam; beam extraction electromagnets adapted to adjust their respective quantities of magnetic excitation at the time of extraction of a charged particle beam and operate to draw out a charged particle beam in a resonant region located off a stable region of charged particle beams; and a beam deflector for beam extractions adapted to draw out the beam extracted from the resonant region to the outside; a pre-accelerator arranged at the inner side of the circular accelerator to accelerate the beam to be injected into the beam deflector for beam injections; and an irradiation device arranged at the outer side of the circular accelerator to irradiate the beam extracted by the beam deflector for beam extractions onto a target of irradiation.

Further, according to another embodiment, there is provided a particle beam therapy apparatus comprising: a circular accelerator having: a beam deflector for beam injections adapted to inject a beam; beam bending electromagnets for forming a circulation orbit by causing the beam injected from the beam deflector for beam injections to circulate; orbit adjusting electromagnets for adjusting the orbit of an injected beam adapted to shift the position of each injected beam relative to the center of the circulation orbit of the beam; beam extraction electromagnets adapted to adjust their respective quantities of magnetic excitation at the time of extraction of a charged particle beam and operate to draw out a charged particle beam in a resonant region located off a stable region of charged particle beams; and a beam deflector for beam extractions adapted to draw out the beam extracted from the resonant region to the outside; a pre-accelerator arranged at the outer side of the circular accelerator to accelerate the beam to be injected into the beam deflector for beam injections; and an irradiation device arranged at the inner side of the circular accelerator to irradiate the beam extracted by the beam deflector for beam extractions onto a target of irradiation.

Now, embodiments of circular accelerator and particle beam therapy apparatus according to the present invention will be described below by referring to the accompanying drawings.

First Embodiment

Figure 1:
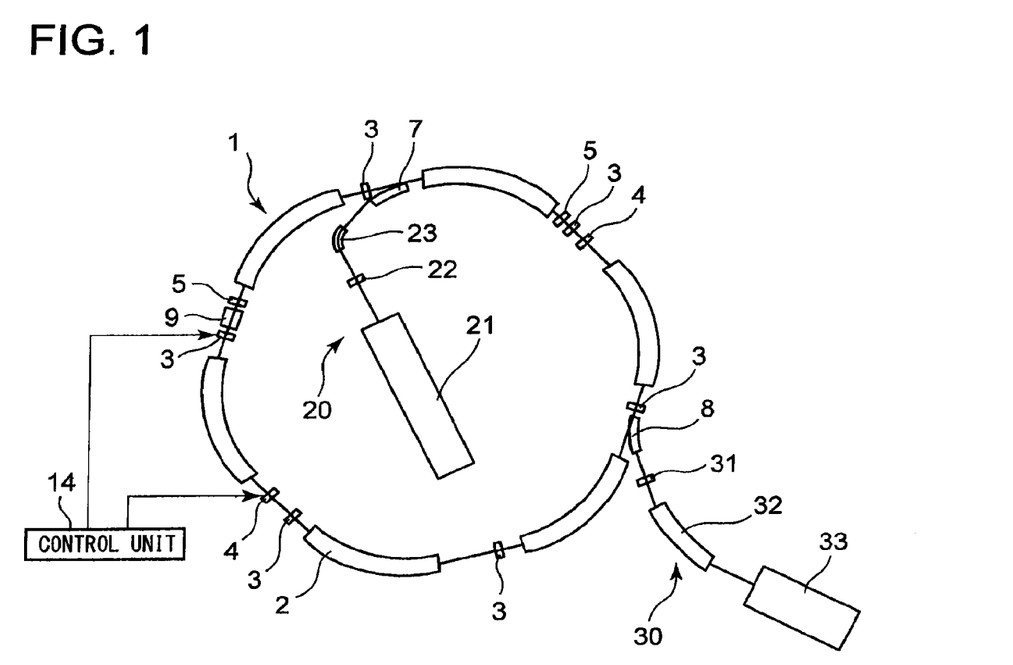
FIG. 1 is a schematic plan view of the first embodiment of a particle beam therapy apparatus according to the present invention.

FIG. 1 is a schematic plan view of the first embodiment of particle beam therapy apparatus. Each of the embodiments will be described below in terms of the use of a charged particle beam for cancer therapy.

As shown in FIG. 1, the charged particle beam therapy apparatus of this embodiment roughly includes a circular accelerator 1, a beam injection system 20 and a beam transport system 30. The circular accelerator 1 of this embodiment is installed on a horizontal plane.

The circular accelerator 1 includes bending electromagnets 2, quadrupole electromagnets 3, sextupole electromagnets 4, orbit adjusting electromagnets 5 that are electromagnets for adjusting the orbit of an injected beam, a beam deflector 7 for beam injections, a beam deflector 8 for beam extractions, a high frequency accelerator device 9 and a control unit 14.

The bending electromagnets 2 deflect the injected charged particle beams to form circulation orbits for the charged particle beams. The quadrupole electromagnets 3 focus/defocus the charged particle beams so as to make the charged particle beams circulate on a stable basis. The sextupole electromagnets 4 excite the third-order resonance of the betatron oscillation of the charged particle beams and form a stable region and a resonant region on a phase space (space defined by a coordinate system of the positions and the angles of the orbits of charged particle beams) by division. The quadrupole. electromagnets 3 and the sextupole electromagnets 4 adjust their respective quantities of magnetic excitation at the time of extracting a charged particle beam and constitute as beam extraction electromagnets that gradually extract the charged particle beams in the resonant region that are located off the stable region of charged particle beams.

During a charged particle beam injection period, the adjustment electromagnets 5 inject charged particle beams at positions that are different relative to the center of circulation orbits at respective injection timings. The beam deflector 7 for beam injections is arranged between the orbit adjusting electromagnets 5 and injects the charged particle beams that are accelerated by a pre-accelerator 21, which will be described hereinafter. The beam deflector 8 for beam extractions deflects charged particle beams to allow them to be emitted. The high frequency accelerator device 9 is a device for generating a high frequency electric field for the purpose of accelerating or decelerating charged particle beams.

The control unit 14 includes a computer, one or more than one memory devices and circuits including various power supply circuits. The control unit 14 controls the quantities of magnetic excitation of the quadrupole electromagnets 3 and the sextupole electromagnets 4 and adjusts the quantities of magnetic excitation of them at the time of extraction of a charged particle beam.

Note that, while the signals from the control unit 14 are sent to all of the quadrupole electromagnets 3 and the sextupole electromagnets 4, only a single arrow is shown to indicate the flow of signals from the control unit 14 to one of the quadrupole electromagnets 3 and also a single arrow is shown to indicate the flow of signals from the control unit 14 to one of the sextupole electromagnets 4 for the purpose of avoiding intricacy.

The beam injection system 20 is arranged at the inner side of the circular accelerator 1 and includes a pre-accelerator 21 for accelerating a charged particle beam before the latter is injected into the deflector 7 for beam injections, a beam injection system quadrupole electromagnet 22 and a beam injection system deflecting electromagnet 23.

The beam transport system 30 is arranged at the outer side of the circular accelerator 1 and includes a beam transport system quadrupole electromagnet 31, a beam transport system bending electromagnet 32 and an irradiation device 33.

With this embodiment, charged particle beams are injected from the inner side of the circular accelerator 1, whereas charged particle beams are emitted to the outer side of the circular accelerator 1.

Now, the advantages of this embodiment will be described below by referring to FIGS. 2 through 5.

Figure 2:
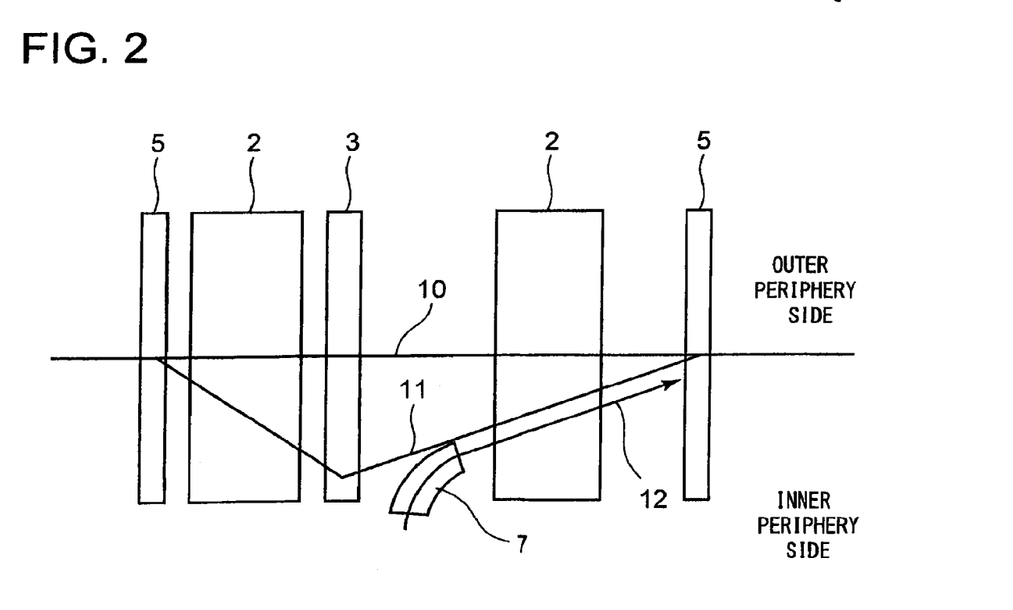
FIG. 2 is a schematic illustration of a multi-turn injection that is an injection from the inner periphery side of the circular accelerator of FIG. 1.
Figure 3:
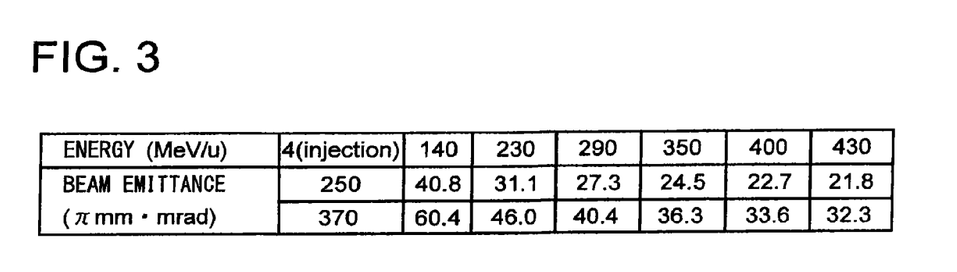
FIG. 3 is a table of the sizes of beams at different beam energy levels (MeV/u) with a beam emittance of 250 $\pi$mm·mrad and a beam emittance of 370 $\pi$mm·mrad that can be observed in the circular accelerator of FIG. 1.
Figure 4:
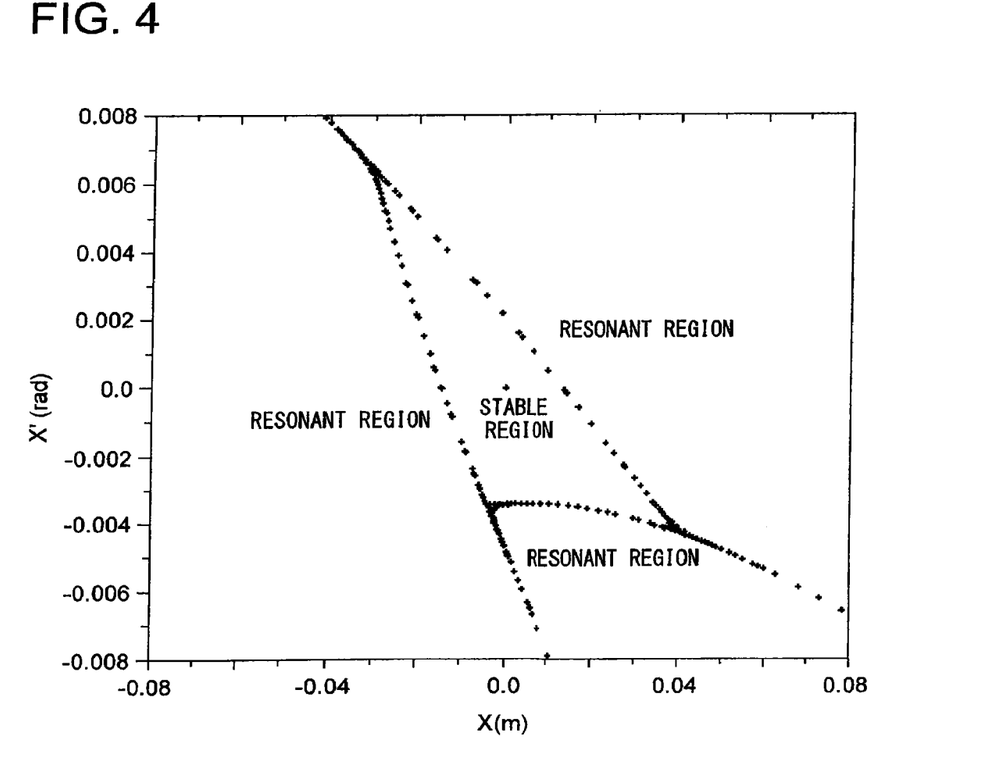
FIG. 4 is a diagram illustrating an increase of beam amplitude obtained by means of third-order resonance in the circular accelerator of FIG. 1.
Figure 5:
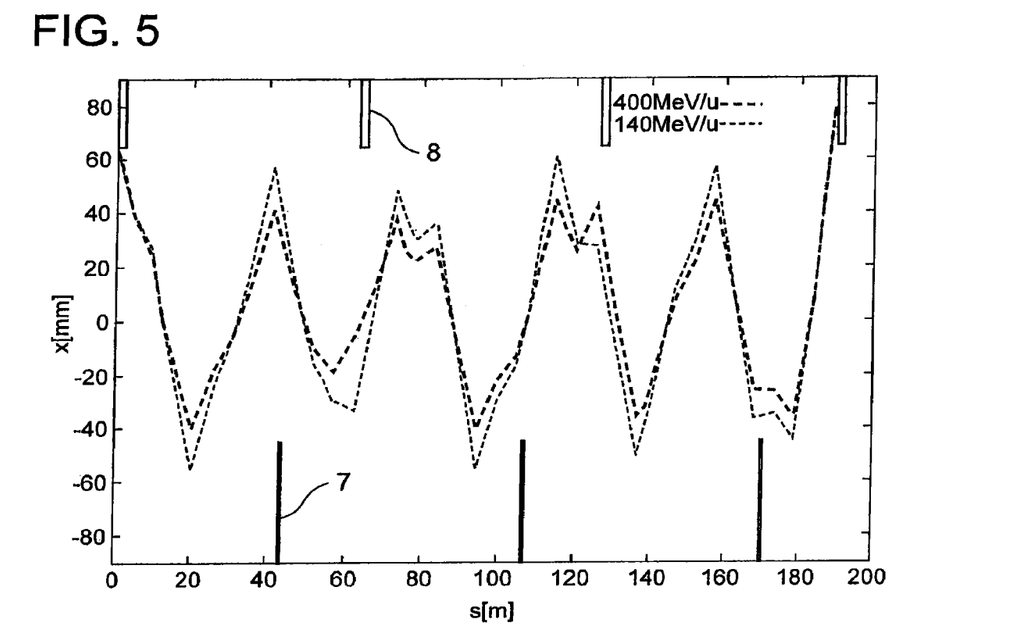
FIG. 5 is a diagram illustrating the trajectories of extraction beams that are injected from the inner side of the circular accelerator of FIG. 1 at energy levels of 400 MeV/u and 140 MeV/u respectively.

FIG. 2 is a schematic illustration of a multi-turn injection that is an injection from the inner periphery side of the circular accelerator of FIG. 1. FIG. 3 is a table of the sizes of beams at different beam energy levels (MeV/u) with a beam emittance of 250 πmm·mrad and a beam emittance of 370

πmm·mrad that can be observed in the circular accelerator of FIG. 1. FIG. 4 is a diagram illustrating of an increase of amplitude obtained by means of the third-order resonance in the circular accelerator of FIG. 1. FIG. 5 is a diagram illustrating of the output beam trajectories with inside injection at energy levels of 400 MeV/u and 140 MeV/u respectively obtained by the circular accelerator of FIG. 1.

Firstly, the operation of this embodiment will be schematically described. The charged particle beam that has been accelerated by the pre-accelerator 21 that is arranged at the inner side of the circular accelerator 1 is forced to be injected from the inner side of the circular accelerator 1 by the beam deflector 7 for beam injections. Then, the charged particle beam is further accelerated by the high frequency accelerator device 9 until the charged particle beam acquires the necessary quantity of energy. Subsequently, the charged particle beam is extracted to the outer side of the circular accelerator 1 by the beam deflector 8 for beam extractions.

Now, the operation of this embodiment will be described below in greater detail.

As shown in FIG. 2, when a charged particle beam is injected into the circular accelerator 1, an injection bump orbit 11 is formed by means of the orbit adjusting electromagnets 5. The injection bump orbit 11 is an orbit formed by shifting the central orbit 10 of circulating beams to the inner periphery side at which the beam deflector 7 for beam injections is arranged by means of the orbit adjusting electromagnets 5.

While the charged particle beam is still being injected, the injection bump orbit 11 is shifted from the position of the beam deflector 7 for beam injections to the position of the central orbit 10. Thus, as a result of injecting charged particle beams, while reducing the quantity of magnetic excitation of the orbit adjusting electromagnets 5, the charged particle beams can be injected to different respective positions at different injection timings. Then, as a result the beam intensities can be raised. This injection method is known as multi-turn injection.

Referring to FIG. 2, the larger the difference (gap) between the injection bump orbit 11 and the orbit of the injected charged particle beam 12 at the time of injecting charged particle beams, the greater the beam amplitude relative to the central orbit 10. Therefore, the beam amplitude is increased as the end of magnetic excitation of the orbit adjusting electromagnets 5 comes closer to make it difficult for the injected charged particle beam to provide a sufficient clearance relative to the beam deflector 7 for beam injections. In other words, charged particle beams that collide with the beam deflector 7 for beam injections disappear and hence the largest size of injected charged particle beams is determined by the position where the beam deflector 7 for beam injections is arranged.

After the injection of the charged particle beam, the charged particle beam is accelerated by the high frequency accelerator device 9 so that its beam size is reduced so as to correspond to its energy by adiabatic damping.

FIG. 3 shows the beam sizes of charged particles that are injected with energy of 4 MeV/u and accelerated by the circular accelerator 1. More specifically, FIG. 3 shows the sizes of beams, each of which is injected with energy of 4 MeV/u, at different beam energy levels (MeV/u) with a beam emittance of 250 πmm·mrad and a beam emittance of 370 πmm·mrad that can be observed after acceleration in the circular accelerator 1 of FIG. 1. The expression of "beam emittance" refers to the area that a charged particle beam occupies on a phase space.

As shown in FIG. 3, when the beam emittance of a charged particle beam is 250 πmm·mrad, as the charged particle beam is accelerated to show energy of 140 Me/u, the beam emittance of the beam becomes equal to 40.8 πmm·mrad. Similarly, when the beam emittance of a charged particle beam is 370 πmm·mrad, as the charged particle beam is accelerated to show energy of 140 MeV/u, the beam emittance of the beam becomes equal to 60.4 πmm·mrad.

Furthermore, when the beam emittance of a charged particle beam is 250 πmm·mrad, as the charged particle beam is accelerated to show energy of 430 MeV/u, the beam emittance of the beam becomes equal to 21.8 πmm·mrad. Similarly, when the beam emittance of a charged particle beam is 370 πmm·mrad, as the charged particle beam is accelerated to show energy of 430 MeV/u, the beam emittance of the beam becomes equal to 32.3 πmm·mrad.

Thus, it will be seen that, as the beam energy of a charged particle beam rises, the beam emittance thereof falls and hence the beam size thereof becomes smaller.

At the time of extraction of a charged particle beam, the quantities of magnetic excitation of the quadrupole electromagnets 3 and those of the sextupole electromagnets 4 are adjusted respectively by the control unit 14. By doing so, the charged particle beam is brought closer to an unstable state that is referred to as resonant state and the area of the stable region of the beam that is circulating is reduced. The amplitude of a charged particle beam in a resonant region that is driven off the stable region is increased. As a result of the increased amplitude, the charged particle beam ultimately expands to the position of the beam deflector 8 for beam extractions that is arranged at the outer periphery side of the circular accelerator 1 and then drawn out to the outside. This technique is known as a slow extraction technique.

FIG. 4 schematically illustrates the state where the amplitude of a charged particle beam is increased by means of third-order resonance on a phase space. In FIG. 4, the horizontal axis shows a direction that is perpendicular to the travelling direction of the charged particle beam in a horizontal direction (the direction of the X-axis) and the vertical axis is the X'-axis showing the differential values obtained by differentiating the shift of a charged particle beam in the X-axis direction by the shift in the travelling direction of the beam.

Particle beams can be divided into those that are in a stable region and those that are in a resonant region on a transversal phase space as illustrated in FIG. 4 (where the horizontal axis is the X-axis and the vertical axis is the X'-axis) due to the third-order resonance of betatron oscillations of a large number of particles circulating in the circular accelerator 1 and the perturbation of the sextupole magnetic fields of the sextupole electromagnets 4 relative to the large number of particles. Since the outside of the stable region for particle beams that is shown as triangle in FIG. 4 is a resonant region, the betatron amplitude of particles that get into the resonant region rises and hence those particles are drawn out from the circular accelerator 1 by the beam deflector 8 for beam extractions.

Then, the charged particle beam drawn out from the circular accelerator 1 is transported to the irradiation device 33 by way of a beam transport system quadrupole electromagnet 31 and a beam transport system bending electromagnet 32. The charged particle beam is then irradiated from the irradiation device 33 onto the affected area of the patient for cancer therapy.

FIG. 5 is a schematic illustration of the last three circulations of charged particle beams that are injected from the inner side of the circular accelerator 1, accelerated to energy levels of 400 MeV/u and 140 MeV/u respectively and drawn out by the beam deflector 8 for beam extractions arranged at the outer side of the circular accelerator 1. In FIG. 5, the horizontal axis shows the length of the three circulations and the vertical axis shows the distance from the center of the circular accelerator 1.

As shown in FIG. 5, the position of arrangement of the beam deflector 8 for beam extractions is located at the side of the orbit closest to the center within the range that is free from interference relative to the injected charged particle beam.

Assume here that the highest energy level is 400 MeV/u. Then, as charged particle beams are injected from the inner side and output to the outer side of the circular accelerator 1, a sufficient clearance is provided for the trajectories of emitted beams without interfering with the beam deflector 7 for beam injections and charged particle beams can be output on a stable basis between the highest energy level of 400 MeV/u and the energy level of 140 MeV/u, which is less than a half of the highest, energy level.

When an instance where charged particle beams are injected from the outer side of the circular accelerator 1 and output to the outer side of the circular accelerator 1 is compared with the above-described instance where charged particle beams of the same number are injected from the inner side of the circular accelerator 1 and output to the inner side of the circular accelerator 1, a greater number of charged particle beams interfere and collide with the beam deflector 7 for beam extractions in a low energy region that allows large beam sizes and disappear in the former instance. Thus, a sufficient clearance cannot be secured for output beam trajectories and hence charged particle beams cannot be output on a stable basis.

Figure 6:
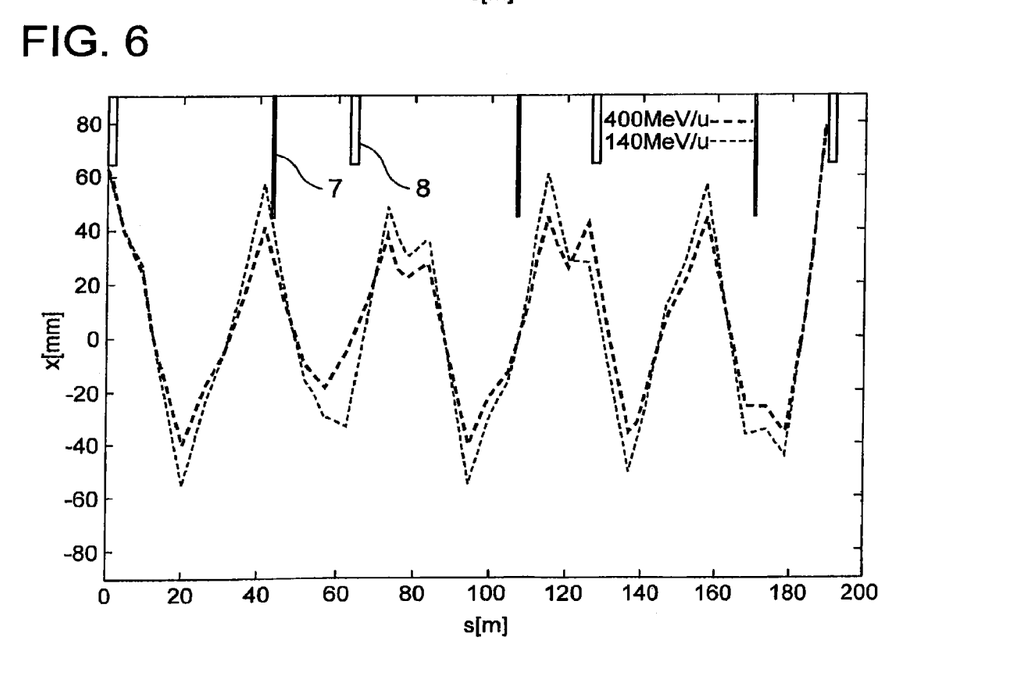
FIG. 6 is a diagram illustrating the trajectories of extraction beams that are injected from the outer side of the circular accelerator of FIG. 1 at energy levels of 400 MeV/u and 140 MeV/u respectively obtained in Comparative Example of the first embodiment.

FIG. 6 is a schematic illustration of the last three circulations of charged particle beams that are injected from the outer side of the circular accelerator 1, accelerated to energy levels of 400 MeV/u and 140 MeV/u respectively and drawn out by the beam deflector 8 for beam extractions arranged at the outer side of the circular accelerator 1.

As shown in FIG. 6, with the arrangement of injecting a charged particle beam from the outer side of the circular accelerator 1, a sufficient clearance cannot be secured for the output beam trajectory relative to the beam deflector 7 for beam injections when the charged particle beam is output with energy that is less than a half of the largest energy. In short, charged particle beams cannot be output on a stable basis for extraction with this arrangement.

In other words, if the largest energy is 400 MeV/u with the arrangement of injecting a charged particle beam from the outer side of the circular accelerator 1, a charged particle beam that is output with energy of 140 MeV/u, which is less than a half of the largest energy, interferes with the beam deflector 7 for beam injections so that a sufficient clearance cannot be secured for the output beam trajectory. In short, charged particle beams cannot be output for extraction on a stable basis with this arrangement.

Therefore, with this embodiment, a charged particle beam is injected from the inner side of the circular accelerator 1 and output to the outer side of the circular accelerator 1. With this arrangement, the circular accelerator 1 can be made very compact and output charged particle beams over a wide range of energy for extraction without damaging the stability of the charged particle beams it handles.

Then, as a result, this embodiment can stably provide charged particle beams over a wide range of energy. Therefore, when it is employed as a particle beam therapy apparatus for irradiating a charged particle beam to the affected area of a patient to be treated, the trajectory of the irradiated beam in the body of the patient can be adjusted over a wide range according to the body part of the patient that needs to be irradiated with the beam and the depth from the body surface of the body part.

Second Embodiment

Figure 7:
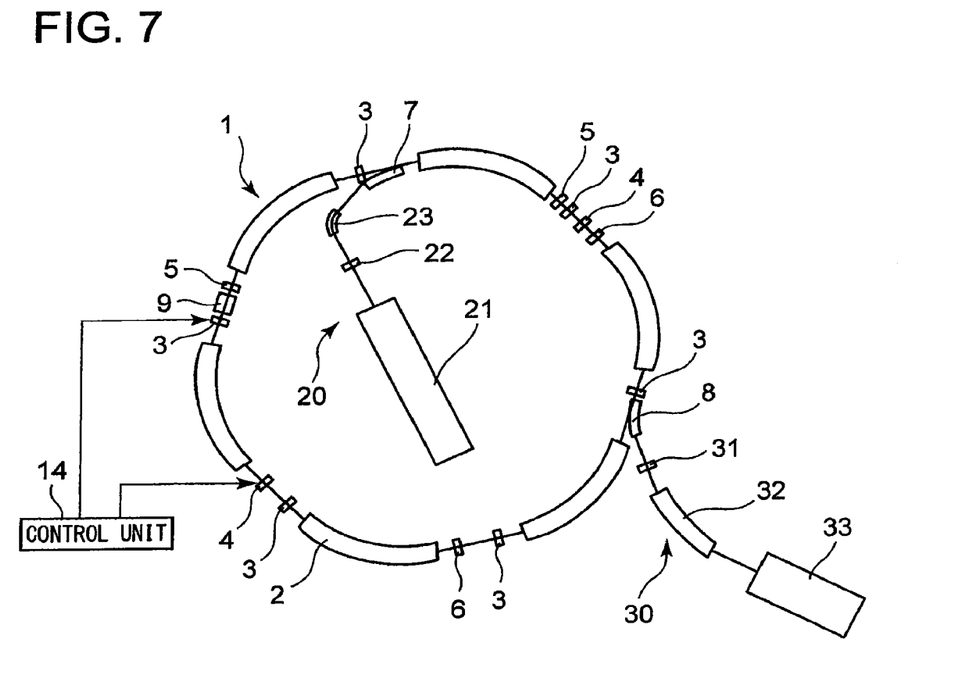
FIG. 7 is a schematic plan view of the second embodiment of particle beam therapy apparatus according to the present invention.

FIG. 7 is a schematic plan view of the second embodiment of particle beam therapy apparatus. Note that the components of this embodiment that are the same as those of the first embodiment are denoted respectively by the same reference symbols and will not be described repeatedly. This statement also applies to all the other embodiments.

As shown in FIG. 7, this embodiment differs from the first embodiment in that two or more than two orbit adjusting electromagnets 6 are arranged upstream and downstream of the beam deflector 8 for beam extraction as viewed in the sense of circulation of charged particle beams so as to constitute as electromagnets for adjusting the orbit of a charged particle beam to be extracted in addition to the components of the first embodiment. These orbit adjusting electromagnets 6 magnetically excite a charged particle beam when the charged particle beam is output for extraction. With this embodiment, the beam orbit can be shifted and hence the charged particle beam is brought closer to the outer side at the position of the beam deflector 8 for beam extractions so as to form an extraction bump trajectory for taking out the charged particle beam.

As described above, with this embodiment, the closed orbit of the charged particle beam to be drawn out is shifted by arranging two or more than two orbit adjusting electromagnets 6 upstream and downstream of the beam deflector 8 for beam extractions. Then, as a result, the charged particle beam can be introduced into the beam deflector 8 for beam extractions with ease. All the remaining components and advantages of this embodiment are the same as those of the first embodiment and hence will not be described repeatedly here.

Note that the arrangement of this embodiment can also be applied to the first embodiment. When it is applied to the first embodiment, the orbit adjusting electromagnets 6 shifts and hence brings the beam orbit closer to the inner side of the circular accelerator 1 at the position of the beam deflector 8 for beam extractions to form an extraction bump trajectory for taking out the charged particle beam. When the first embodiment is arranged in this way, it provides advantages similar to those of the second embodiment.

Third Embodiment

In the first and second embodiments, the circulating beams in the circular accelerator 1 show a certain distribution pattern and those having energy greater than the center energy form respective closed orbits that are shifted to the outer periphery side, whereas those having energy smaller than the center energy form respective closed orbits that are shifted to the inner periphery side. As the momentum dispersion function of the charged particle beams that are injected into the circular accelerator 1 is made to show a positive value, charged particle beams having large energy are injected to the outer side of the closed orbits, while charged particle beams having small energy are injected to the inner side of the closed orbits so that the dispersion of amplitude of injected beams that is attributable to the dispersion of energy can be confined.

Meanwhile, when a charged particle beam is injected from the inner side in a state where the momentum dispersion function shows a value of nil, the momentum dispersion function becomes to show a positive value. On the other hand, when a charged particle beam whose momentum dispersion function is equal to nil passes a quadrupole electromagnet 3, the value of the momentum dispersion function remains nil.

It is known that the size of a charged particle beam can be controlled within a certain range both in the horizontal direction and in the vertical direction by using three or more than three quadrupole electromagnets 3. Thus, a beam line that makes the value of the momentum dispersion equal to nil is provided upstream relative to the position for injection from the inner side and three or more than three quadrupole electromagnets 3 are arranged. Then, as a result, the momentum dispersion at the position where a charged particle beam is output from the beam deflector 7 for beam injections can be adjusted only for the beam size, while the positive fixed value determined by the three or more than three quadrupole electromagnets is left intact. Thus, the conditions for a beam injection can be optimized with ease.

Other Embodiments

While some embodiments of the present invention are described above, they are presented only as exemplar embodiments and not intended to limit the scope of the present invention by any means. The present invention can be embodied in various different ways and the above-described embodiments can be modified, altered and/or combined in various different ways without departing from the spirit and scope of the invention. Therefore, those modified embodiments are found within the scope of the present invention. The scope of the following claims is to be accorded the broadest interpretation so as to encompass all such modifications and equivalent structures and functions.

For example, in each of the above-described embodiments, the clearance relative to the beam deflector 7 for beam injections can be further increased by modifying the quantity of magnetic excitation of the deflecting electromagnets 2 for forming a circulation orbit at the timing of outputting a charged particle beam for extraction to shift all the closed orbits.

Additionally, in each of the above-described embodiments, the closed orbits can be moved away from the beam deflector 7 for beam injections at the time of outputting a charged particle beam for extraction by magnetically exciting the orbit adjusting electromagnets 5 that are operated for the injection of the beam to the polarity opposite to the polarity at the time of the injection. Then, as a result, the clearance can be broadened to a greater extent.

Furthermore, in each of the above-described embodiments, at the time of injecting a charged particle beam, the introduction of a charged particle beam is suspended while shifting the injection bump orbit. As the initial beam size is reduced in this way, the charged particle beam can be handled with smaller energy at the time of outputting the charged particle beam for extraction so that the range of energy that is available for extractions of charged particle beams can be broadened.

Still additionally, each of the above embodiments is described in terms of being applied to a charged particle beam therapy apparatus with a beam transport system 30. However, the present invention is by no means limited to such applications. For example, charged particle beams at high energy level can find applications in various scientific and industrial fields including physical experiments.

Finally, each of the above embodiments is described in terms of using charged particle beams for cancer therapy. However, the present invention is by no means limited thereto. For example proton beams can also be used for cancer therapy.

What is claimed is:

1. A circular accelerator comprising:
   a beam deflector for receiving beam injections and deflecting the beam;
   beam bending electromagnets for forming a circulation orbit by causing the beam injected from the beam deflector for beam injections to circulate;
   orbit adjusting electromagnets for adjusting orbit of an injected beam adapted to shift the position of each injected beam relative to center of the circulation orbit of the beam;
   beam extraction electromagnets adapted to adjust their respective quantities of magnetic excitation at time of extraction of a charged particle beam and operate to draw out a charged particle beam in a resonant region located off a stable region of charged particle beams; and
   a beam deflector for beam extractions adapted to draw out the beam extracted from the resonant region to outside;
   the circular accelerator being adapted to inject the beam from inner side and extract the beam to outer side of the circular accelerator.

2. The circular accelerator according to claim 1, further comprising:
   orbit adjusting electromagnets adapted to bring the orbit of a beam to be extracted closer to the outer side of the circular accelerator and extract the beam at the time of extracting the beam.

3. The circular accelerator according to claim 1, wherein the beam to be extracted is drawn out by modifying the quantity of magnetic excitation of the beam bending electromagnets and shifting the central orbit of the beam at the time of extracting the beam.

4. The circular accelerator according to claim 1, wherein, at the time of a beam extraction, the orbit adjusting electromagnets for adjusting the orbit of an injected beam is magnetically excited to opposite polarity and the beam is extracted while increasing clearance relative to the beam deflector for beam injections.

5. The circular accelerator according to claim 1, wherein, at the time of a beam injection, the injection of the beam is suspended while shifting the beam relative to the center of the circulation orbit of the beam by means of the orbit adjusting electromagnets for adjusting the orbit of an injected beam so as to reduce the initial beam size.

6. The circular accelerator according to claim 1, wherein the momentum dispersion function of the beam deflector for beam injections is made to show a positive value at the time of a beam injection.

7. A circular accelerator comprising:
   a beam deflector for beam injections adapted to inject a beam;
   beam betiding electromagnets for forming a circulation orbit by causing a beam injected from the beam deflector for beam injections to circulate;
   orbit adjusting electromagnets for adjusting orbit of an injected beam adapted to shift the position of each injected beam relative to center of the circulation orbit of the beam;
   beam extraction electromagnets adapted to adjust their respective quantities of magnetic excitation at time of extraction of a charged particle beam and operate to draw out a charged particle beam in a resonant region located off a stable region of charged particle beams; and
   a beam deflector for beam extractions adapted to draw out the beam extracted from the resonant region to outside;

the circular accelerator being adapted to inject the beam from outer side and extract the beam to inner side of the circular accelerator.

8. The circular accelerator according to claim 7, further comprising:

orbit adjusting electromagnets adapted to bring the orbit of the beam to be extracted closer to the inner side of the circular accelerator and extract the beam at the time of extracting the beam.

9. The circular accelerator according to claim 7, wherein the beam to be extracted is drawn out by modifying the quantity of magnetic excitation of the beam bending electromagnets and shifting the central orbit of the beam at the time of extracting the beam.

10. The circular accelerator according to claim 7, wherein, at the time of a beam extraction, the orbit adjusting electromagnets for adjusting the orbit of an injected beam is magnetically excited to opposite polarity and the beam is emitted while increasing clearance relative to the beam deflector for beam injections.

11. The circular accelerator according to claim 7, wherein, at time of a beam injection, the injection of the beam is suspended while shifting the beam relative to the center of the circulation orbit of the beam by means of the orbit adjusting electromagnets for adjusting the orbit of an injected beam so as to reduce the initial beam size.

12. The circular accelerator according to claim 7, wherein the momentum dispersion function of the beam deflector for beam injections is made to show a positive value at the time of a beam injection.

13. A particle beam therapy apparatus comprising:

a circular accelerator having:

a beam deflector for beam injections adapted to inject a beam;

beam bending electromagnets for forming a circulation orbit by causing a beam injected from the beam deflector for beam injections to circulate;

orbit adjusting electromagnets for adjusting orbit of an injected beam adapted to shift the position of each injected beam relative to center of the circulation orbit of the beam;

beam extraction electromagnets adapted to adjust their respective quantities of magnetic excitation at time of extraction of a charged particle beam and operate to draw out a charged particle beam in a resonant region located off a stable region of charged particle beams; and a beam deflector for beam extractions adapted to draw out the beam extracted from the resonant region to outside;

a pre-accelerator arranged at inner side of the circular accelerator to accelerate the beam to be injected into the beam deflector for beam injections; and an irradiation device arranged at outer side of the circular accelerator to irradiate the beam extracted by the beam deflector for beam extractions onto a target of irradiation.

14. A particle beam therapy apparatus comprising:

a circular accelerator having:

a beam deflector for beam injections adapted to inject a beam;

beam bending electromagnets for forming a circulation orbit by causing the beam injected from the beam deflector for beam injections to circulate;

orbit adjusting electromagnets for adjusting orbit of an injected beam adapted to shift the position of each injected beam relative to center of the circulation orbit of the beam;

beam extraction electromagnets adapted to adjust their respective quantities of magnetic excitation at time of extraction of a charged particle beam and operate to draw out a charged particle beam in a resonant region located off a stable region of charged particle beams; and a beam deflector for beam extractions adapted to draw out the beam extracted from the resonant region to outside;

a pre-accelerator arranged at outer side of the circular accelerator to accelerate the beam to be injected into the beam deflector for beam injections; and an irradiation device arranged at inner side of the circular accelerator to irradiate the beam extracted by the beam deflector for beam extractions onto a target of irradiation.

* * * * *